United States Patent
Berlad et al.

(10) Patent No.: US 6,369,389 B1
(45) Date of Patent: Apr. 9, 2002

(54) REAL-TIME COMPTON SCATTER CORRECTION

(75) Inventors: Gideon Berlad; Dov Maor, both of Haifa (IL)

(73) Assignee: GE Medical Systems Israel, Ltd., Tirat-Hacarael (IL)

( * ) Notice: Subject to any disclaimer, the term of this patent is extended or adjusted under 35 U.S.C. 154(b) by 0 days.

(21) Appl. No.: 09/308,376

(22) PCT Filed: Nov. 24, 1996

(86) PCT No.: PCT/IL96/00162

§ 371 Date: May 14, 1999

§ 102(e) Date: May 14, 1999

(87) PCT Pub. No.: WO98/23973

PCT Pub. Date: Jun. 4, 1998

Related U.S. Application Data

(63) Continuation-in-part of application No. 08/562,375, filed on Nov. 24, 1995, now Pat. No. 5,689,115.

(51) Int. Cl.[7] .................................................. G01T 1/20
(52) U.S. Cl. ............................ 250/363.07; 250/363.02
(58) Field of Search ....................... 250/363.07, 363.02, 250/363.03, 363.04

(56) References Cited

U.S. PATENT DOCUMENTS

| | | |
|---|---|---|
| 3,011,057 A | 11/1961 | Anger |
| 4,424,446 A | 1/1984 | Inbar et al. |
| 4,780,823 A | 10/1988 | Stoub et al. |
| 4,839,808 A | 6/1989 | Koral et al. |
| 5,276,615 A | 1/1994 | Edmond et al. |
| 5,285,072 A | 2/1994 | Klingenbeck et al. |
| 5,293,195 A | 3/1994 | Berlad et al. |
| 5,345,082 A | 9/1994 | Engdahl et al. |
| 5,371,362 A | 12/1994 | Mestais et al. |
| 5,434,414 A | 7/1995 | Berlad et al. |
| 5,438,202 A | 8/1995 | Matanzon et al. |
| 5,466,939 A * | 11/1995 | Kumazawa et al. ... 250/363.04 |
| 5,508,524 A | 4/1996 | Goldberg et al. |
| 5,633,500 A * | 5/1997 | Morgan et al. ........ 250/363.07 |
| 5,648,659 A * | 7/1997 | Bourguignon et al. . 250/363.04 |
| 5,689,115 A | 11/1997 | Balan et al. |
| 5,793,045 A * | 8/1998 | DiFilippo et al. ...... 250/363.03 |

FOREIGN PATENT DOCUMENTS

EP    0 261 696    3/1988

\* cited by examiner

Primary Examiner—Constantine Hannaher
Assistant Examiner—Otilia Gabor
(74) Attorney, Agent, or Firm—Fenster & Company Patent Attorneys, Ltd.

(57) ABSTRACT

A method of reducing artifacts caused by generation of unwanted photons by scattering (e.g., Compton scattered photons) in which a detected event is spatially convoluted with a spatial filter function. The filter function has a distribution of weights within the filter function that is dependent on the energy of the event for a same primary event energy.

16 Claims, 5 Drawing Sheets

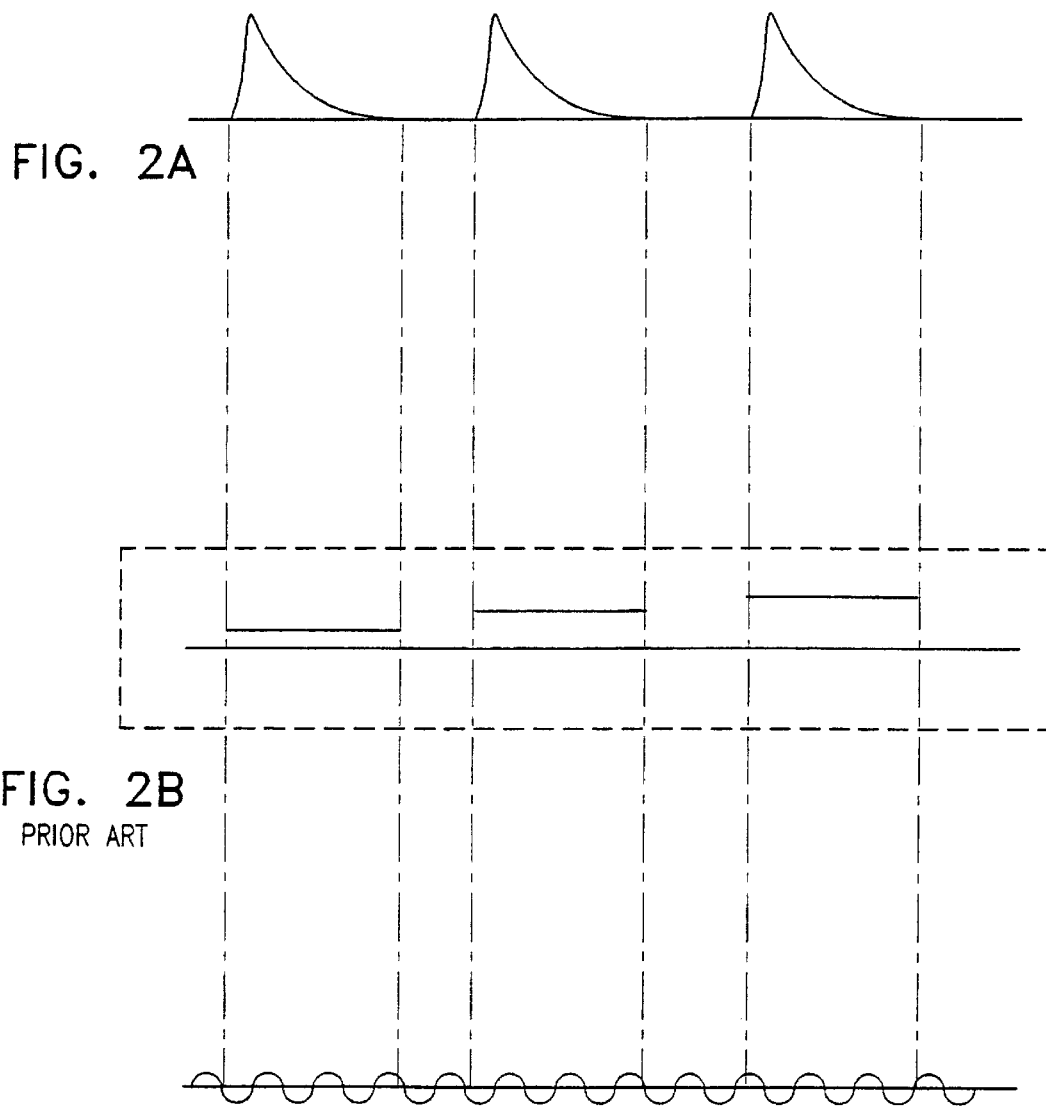
FIG. 2A
FIG. 2B
PRIOR ART
FIG. 2C
FIG. 2D

REAL-TIME COMPTON SCATTER CORRECTION

RELATED APPLICATIONS

This application is a U.S. National filing of PCT application PCT/IL96/00162, filed Nov. 24, 1996 which is a continuation in part of U.S. patent application Ser. No. 08/562,375, filed Nov. 24, 1995, now U.S. Pat. No. 5,689,115.

FIELD OF THE INVENTION

This invention is related to the art of nuclear medicine imaging and in particular to digital nuclear medicine systems.

BACKGROUND OF THE INVENTION

This application is an improvement of a co-pending unpublished U.S. patent application Ser. No. 08/562,375, filed Nov. 24, 1995, titled "An Advanced Nuclear Medicine System." FIG. 1 shows a block diagram of a generalized prior art nuclear medicine system 550 used to image a patient 504. System 550 is used to generate images of radio-nuclide concentrations in patient 504. Patient 504 is injected with a radio-pharmaceutical which usually forms at least a concentration 506 in portions of patient's 504 anatomy. Patient 504 is placed in an examination area (not shown) so that a scintillation detector crystal 500 can detect gamma radiation emitted by radio-pharmaceuticals in concentration 506.

In nuclear medicine imaging, gamma rays emitted by radioactive materials are treated as a particle phenomenon. Each measured photon corresponds to one radiation event and the number of radiation events from a region reflects the concentration of the radio-active material in that region. However, the energy of the events indicates whether they have traveled directly from concentration 506 or have their origin in a different region of the anatomy and have been scattered.

As a result, nuclear medicine system design emphasizes filtering real radiation events from scattered events (whose origin is unknown). Due to the weak interaction between gamma-rays and matter and the desire to use low dosages of radioactivity, gamma-rays are not captured on film or with detectors such as used in X-ray CT systems. Gamma radiation emitted by the radio-pharmaceutical interacts with detector crystal 500 to produce minuscule flashes of light. Each radiation event generates one light flash in detector 500. Several of a plurality of photomultipliers 502 detect this flash of light and generate an electrical current responsive to the intensity of light sensed by the individual photomultiplier. The contributions of photomultipliers 502 are added together to determine the amount of energy in the event and, hence, its validity. In addition, the location of the event is determined by analyzing the signals from each of photomultipliers 502.

Each photomultiplier 502 has its own signal processing circuit. The electric current produced by each photomultiplier 502 is amplified by an amplifier 508 and is then delayed and shaped by a shaper/delayer 512. The purpose of shaping the signal is to compress the signal. Most nuclear medicine systems are event triggered and event blocked. Thus, when an event is registered, the system processes it and no further events can be registered or processed while the first event is being processed. Compression shortens the time extent of an event so that processing time (integration) is shorter and the maximum event rate is higher.

Typically, shaper/delayer 512 is triggered only if the radiation event has a total energy which is within a specific wide energy window. Otherwise, the measured event is probably an uninteresting scattering event and is discarded. The outputs of all of amplifiers 508 are summed by an adder 510. The sum calculated by adder 510 is used by a gating unit 514 to selectably trigger shaper/delayer 512 responsive to the sum. If the sum is within a preset range of values, gating unit 514 triggers shaper/delayer 512 to process the radiation event. It should be noted that the total energy of the event is approximately determined at this stage. Using the delay, full scale integration eventually starts only if the approximate energy falls within predefined limits.

An integrator 516 integrates the signal produced by shaper/delayer 512 to find the total energy associated with the radiation event detected by one specific photomultiplier 502. An important result of the integration is noise reduction.

As in many measurement systems, even when there is no event being measured, there is a parasitic DC level, usually referred to as a base-line voltage. This base-line voltage is typically subtracted from the signal before integration. Otherwise, the integrated signal contains a large (unknown) contribution from the base-line. This process is called base line restoration.

The individual detector circuits are connected to a single event processing unit 519. A sequencer 517 multiplexes the results from all of integrators 516 and passes them serially to event processing unit 519.

Typically, the analog signal is converted to a digital signal after integration. Conversion of analog signals to digital signals is problematic for the short pulse durations typical of nuclear medicine imaging. In particular, analog to digital converters tend to:

(a) have relatively low resolutions;
(b) be non-linear in their response; and
(c) have response curves which vary between converters and, for a single converter, with time.

U.S. Pat. No. 5,371,362, the disclosure of which is incorporated herein by reference, discloses a base line measurement and correction system. The output signal of each photomultiplier is sampled by an analog-to-digital (A/D) converter and analyzed to determine the values of the base-line voltage between radiation events. The determined base line voltage is subtracted from the sampled signals prior to integration to yield base-line corrected signals. Also disclosed is the addition of a sliding scale voltage to the photomultiplier output signal. A sliding scale voltage is generated by the system responsive to the amplitude of the sampled signal. The sliding-scale voltage is added to the signal from the photomultipliers so that its amplitude is within the linear range of the analog to digital converter.

In the APEX system (Elscint LTD., Haifa, Israel), a sliding scale signal having a cycle time which is 64 events long is added to the analog signal before conversion. Each step of the sliding scale is equivalent to about one LSB (least significant bit) of the A/D converter. After A/D conversion, A digital value corresponding to the sliding scale analog value is subtracted from the digitized value of the energy of the event. The sliding scale is event driven, thus, the sliding scale signal is constant for the duration of each event and varies by one level between events. FIG. 2A shows an analog signal generated by photomultiplier tubes 502 and FIG. 2B shows a sliding scale signal as described herein.

Referring again to FIG. 1, event processing starts with determining the X-Y position of the radiation event on detector head 500. Only strong signals are useful for this determination. Thus, a selector 518 selects only those integration results which are above a threshold. A normalizer 520 normalizes the selected results to make their sum a constant and a position calculator 522 uses the normalized results to perform Anger arithmetic and calculate the position of the radiation event in the plane of detector 500.

Typically, some of the Anger arithmetic calculations are performed by an array of weighted resistors. These resistors are connected directly to photomultipliers 502 and calculate weighted sums of the signals from photomultipliers 502.

Following positioning, the radiation events are corrected for linearity errors, energy errors and variable sensitivity errors by an event corrector 524. Linearity errors are systematic errors in the position calculation by Anger arithmetic. Sensitivity errors are caused by detector 500 having a position dependent sensitivity, i.e., some portions of detector 500 naturally detect more events than others portions, even if all of detector 500 is receiving a uniform event flux. Energy errors are caused by non-detection of some of the light generated by an event, e.g., light passing through the spaces between photomultiplier tubes 502. Thus, similar events are acquired by system 550 as having dissimilar energy levels. Usually, the events whose energy level is not within a position dependent narrow window are rejected by system 550. In some nuclear medicine systems, events are corrected only after non-events are rejected.

If it is desired to transform the image, (e.g., enlarging it), there are two possible solutions. Corrector 524 can be configured to perform the transformation. However, all of the geometric transformations (linearity corrections and others) are usually performed as one step using a single table. Thus, when the desired transformation changes, the geometric transformation table in corrector 524 must be recalculated, which is time consuming.

Alternatively, the transformations can be performed on the final image. However, the quality of the transformed image is lower than the quality of the original image, due to aliasing effects.

Image generation by an image processor 526 completes the processing of radiation events so that a completed image can be displayed on a display 528.

U.S. Pat. No. 5,345,082, the disclosure of which is incorporated herein by reference, discloses energy dependent linearity correction. A separate linearity correction map is stored for each of several energy ranges. The positioning of a detected event is corrected using the linearity map which matches the event's energy.

U.S. Pat. No. 5,276,615, the disclosure of which is incorporated herein by reference, mentions a nuclear medicine system wherein the outputs of the photomultiplier tubes are directly sampled by an analog-to-digital converter. Apparently, summing, integration and positioning are performed digitally on the sampled outputs.

U.S. Pat. No. 4,780,823 to Stoub et al., the disclosure of which is incorporated herein by reference, describes a Compton scatter correction system in which each event is added to a data matrix as a first value for a central pixel and as a plurality of values for neighboring pixels. A single set of values is used for each type of isotope and/or collimator and/or camera head. This set is weighted with a coefficient which is dependent on the energy of the event.

SUMMARY OF THE INVENTION

It is an object of the present invention to provide a nuclear imaging system having improved image quality. According to a preferred embodiment of the invention, a digital nuclear medicine system includes, a detector unit which generates an analog electrical signal responsive to an impinging radiation event. The analog signal is converted to a digital signal before any steps of:

(a) integrating the signal to provide an energy value for the event; or (b) summing analog signals from a plurality of detectors.

After conversion, the digital signal is baseline restored and the signal is integrated to provide an energy value for the event.

In general, digital processing of signals is faster, more stable, precise and flexible than processing analog signals. Nuclear medicine systems are signal processing intensive, thus, a digital processing system is advantageous. However, the step of converting analog signals to their digital counterparts usually degrades the signal resolution and adds noise. As a result, most prior art nuclear medicine systems optimize their image quality by postponing the A/D conversion until after at least some of the processing is performed using analog circuitry.

Analog to digital conversion has a limited resolution. In a first aspect of the invention, this resolution is enhanced by varying the input signal. For example, if a constant signal having the value of 2.9 is converted (without enhancement) by an analog to digital converter having the resolution of 1, the resulting digital value will be 2, an error of approximately 50%. However, if a periodic signal having the amplitude of 1 is added to the analog signal, the resulting analog value will cycle between 1.9 and 3.9. If this new signal is sampled and converted several times, the average digital signal will be approximately 2.9.

In a first preferred embodiment of the present invention, a resolution enhancement signal is added to the analog signal before converting the analog signal to the digital signal. Preferably, the resolution enhancement signal is a time varying cyclical or pseudo-random signal which cycles several times during the detection of a single event and has a precision higher than the resolution of the analog to digital converter. More preferably, the resolution enhancement signal has an amplitude on the order of the resolution of the analog to digital conversion. Preferably, the sum of the resolution enhancement signal over the integration time is zero. Thus, the resolution enhancement signal does not add to the integrated signal and, as a consequence, does not need to be corrected for before integration. In a further preferred embodiment, especially useful when the integration time of the digital signal is not constant, the addition of the resolution enhancement signal is corrected for by subtracting a digital equivalent of the integral of the resolution enhancement signal from the digital signal before restoring the baseline.

The resolution enhancement signal is preferably synchronized to the analog to digital conversion process.

A second limitation of analog to digital converters is that they are not uniformly linear over their acquisition range. These non-uniformities can be corrected by mapping the response of the converter and correcting some of the errors after acquisition. However, even if a converter is mapped to correct for these non-uniformities, when the converter is replaced it must be mapped again. In addition, the linearity of analog-to-digital converters changes over time.

Thus, in a second aspect of the invention, a linearity enhancement signal is added to the analog signal before conversion thereof to the digital signal. The linearity enhancement signal is added in addition to, or alternatively to, the resolution enhancement signal. Preferably, the linearity enhancement signal cycles slowly, such that it approximates a constant signal during the integration time of a single event. Also, the amplitude of the linearity enhancement signal is preferably approximately 5% of the range of the analog to digital converter. The amplitude of the linearity enhancement signal is preferably higher than the resolution of the analog to digital converter, i.e., it is many resolution elements in amplitude.

It should be appreciated that the digital signal that has its base line restored by the base line restorator has a higher precision than the digital signal generated by the analog to digital converter. It should be appreciated that since the linearity enhancement signal varies slowly, the base line restorator treats it as a DC signal so that the base line restorator can generally correct for the linearity enhancement signal without special circuitry and without receiving the linearity enhancement signal as an input. Optionally, a digital equivalent of the linearity enhancement signal is subtracted from the digital signal before base line restoration.

In order to generate an image based on a plurality of radiation events, several steps are preferably performed on each event:

(a) the location of the radiation event is determined;

(b) linearity errors in the positioning of the event are corrected;

(c) errors in the determination of the energy of the event are corrected;

(d) errors in event detection are corrected, for example, errors due to non-uniform sensitivity of the detector;

(e) other positioning errors in the positioning of the event are corrected, for example, errors caused by mechanical misalignment;

(f) the position of the event is transformed using a general geometric transformation, for example, zooming in; and (g) events are assigned to a location in an image plane.

Generally, when more than one of (b), (e) and (f) are performed, they are usually performed using a single transformation map. Alternatively, (e) or (f) are performed on the image plane after (g).

This method has several disadvantages. First, it is time consuming to calculate the single transformation map. Thus, when any of the corrections or transformations in (b), (e) or (f) are changed, event acquisition is delayed until the recalculation is finished. Second, corrections which are time dependent are impossible to perform, since the transformation map is static and the image plane has no time dimension. Third, if a correction is applied to the image plane, the result is only as precise as the resolution of the image plane, which is, in clinical settings, 6–8 bits and does not usually exceed 10 bits.

In a preferred embodiment of the invention (a)–(f) are performed as separate, independent steps on each individual event. Thus, an event is assigned to the image plane only after all the desired transformations and corrections have been applied to it. As a result, each event can have different, non-constant, possibly time based, corrections and transformations applied to it. In addition, the precision of (a)–(e) is as high as that of the calculation system, and is not limited by the image plane resolution.

Preferably, a time-based correction in accordance with a preferred embodiment of the invention, corrects for distortions caused by some radio-pharmaceuticals deteriorating rapidly during a nuclear medicine session. Radiation events which occur later in the session are given higher weights to compensate for this deterioration.

Another preferred non-constant correction is a correction for mechanical misalignment. In a typical tomographic nuclear medicine system, detector assemblies are rotated around a patient. However, the detector assemblies sag as a result of their weight. Also, the center of rotation for the assemblies is not always exactly at the center of the projection plane. In a preferred embodiment of the invention, the error in the position of the event caused by sagging of the camera detectors is corrected by applying an angle based geometric transformation to each event. The center of rotation is also corrected by applying a second geometric transformation to the event. These corrections can be combined in a single geometric transformation.

Yet another preferred non-constant correction is a velocity correction for linear scanning, where a detector scans along the patients body. In a preferred embodiment of the present invention, velocity changes are corrected for by giving each event a position dependent weight, depending on the velocity of the detector at the time the event is acquired.

A common geometrical transformation is converting a fan beam image to a parallel beam image to optimally utilize both detector and image plane area. In a preferred embodiment of the present invention, a small portion of the patients body is imaged using a fan-beam collimator. However, the radiation events are repositioned, before being assigned to the image plane, to simulate the use of a parallel beam collimator. Thus, a high resolution fan-beam acquired image is displayed without the typical distortions caused by the fan beam collimator.

Since each event is provided with a weight, several type of irregularities are correctable by varying the weighting of each event. Sensitivity correction is achieved in a preferred embodiment of the present invention by first mapping the sensitivity uniformity of the detector and, during acquisition, giving each event a (fractional) weight which is dependent on the event's position in the detector.

In a further preferred embodiment of the present invention, Compton scattering artifacts are reduced in real-time on an event-by-event basis. Each event is assigned using an accumulation matrix to a central pixel with a first (energy dependent) weight and to a surrounding region with a second (energy dependent) weight. Preferably, the ratio between the first and second weights is also energy dependent.

If radiation events happen faster than the nuclear medicine system can handle, the events are lost. Preferably, an event counter counts the number of actual events. A higher weight is attached to an event during a period in which the event rate is high.

In another preferred embodiment, events occurring during a short frame time are given a higher weight than events occurring during long frame times. Thus, images having different frame times but similar content, will have similar intensities.

There is therefore provided in accordance with a preferred embodiment of the invention, a method of reducing artifacts caused by unwanted photons having a known energy distribution in a radiation camera which images radiation from primary radiation events, including:

(a) detecting a radiation event;

(b) determining an energy of the event;

(c) determining a location of the event;

(d) convoluting each event on an event-by event basis with a filter function, where the filter function is dependent on the determined energy and on a predetermined energy dependent scatter coefficient of the unwanted photons in the radiation camera; and (e) repeating (a)–(d) for a plurality of events.

There is also provided a method of reducing artifacts caused by unwanted photons having a known energy distribution in a radiation camera which images radiation from primary radiation events, including:

(a) detecting a radiation event;

(b) determining an energy of the event;

(c) determining a location of the event;

(d) convoluting each event on an event-by-event basis with a spatial filter function, which filter function is dependent on the determined energy and where the filter function at one energy is different in more than magnitude from the filter function at a second energy associated with a primary event having the same energy; and (e) repeating (a)–(d) for a plurality of events. Preferably, the filter function has a first portion having a first weight and a second portion having a second weight and the ratio between the first and second weights is energy dependent. Alternatively or additionally, the filter function is dependent on a predetermined energy dependent scatter coefficient of the unwanted photons in the radiation camera.

In a preferred embodiment of the invention, the filter function has a continuous dependence on the energy of the event. Additionally or alternatively, the filter function is predetermined. Additionally or alternatively, the filter function is dependent on the energy of the primary radiation event. Preferably, the primary radiation events are generated by one of at least two different radioactive elements introduced into a patient.

Generally, unwanted photons include Compton scattered photons of a primary event. Alternatively or additionally, the unwanted photons include x-rays generated by the interaction of a primary event with the radiation camera.

There is also provided in accordance with a preferred embodiment of the invention, a nuclear medicine system which images radiation from primary radiation events and which detects unwanted photons having a known energy distribution, including:

an event detector which detects a radiation event;

an event energy and location detector which determines the energy and location of the event; and an unwanted-photon corrector which receives an event energy and location and convolutes the location with an energy dependent filter function, where the filter function is based on a predetermined energy distribution of unwanted photons and on a predetermined system point spread function.

There is further provided in accordance with a preferred embodiment of the invention, a nuclear medicine system which images radiation from primary radiation events and which detects unwanted photons having a known energy distribution, including:

an event detector which detects a radiation event;

an event energy and location detector which determines the energy and location of the event; and an unwanted-photon corrector which receives an event energy and location and convolutes the location with an energy dependent filter function, which filter function is a spatial filter and where the filter function at one element is different in more than magnitude than the filter function at a different energy associated with a primary event having the same energy. Preferably, the filter function includes a first weight and a second weight and the ratio between the first and second weights is energy dependent. Additionally or alternatively, different filter functions are used for different primary event types.

Generally, the unwanted photons include Compton scattered photons of a primary event. Alternatively or additionally, the unwanted photons include x-rays generated by the interaction of a primary event with the radiation camera.

BRIEF DESCRIPTION OF THE DRAWINGS

FIG. 2A is a graph showing a response of a photomultiplier tube to a series of radiation events;

FIG. 2B shows a prior art wave form which is added to the photomultiplier response;

FIGS. 2C–2D are graphs showing various wave forms which are added to the photomultiplier response in various preferred embodiments of the present invention;

DETAILED DESCRIPTION OF THE PREFERRED EMBODIMENTS

Figure 1:
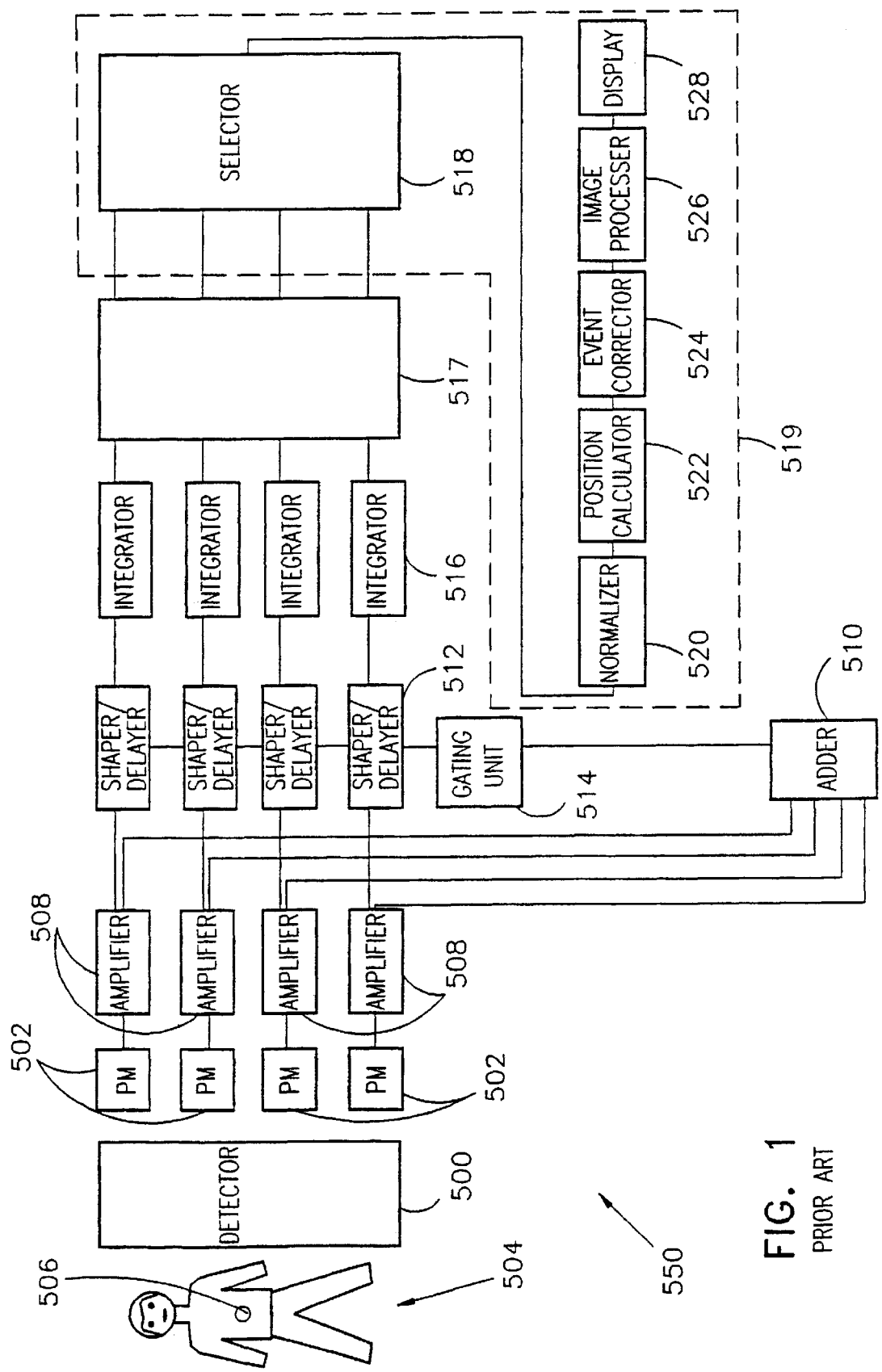
FIG. 1 is a block diagram of a prior art nuclear medicine system.
Figure 3:
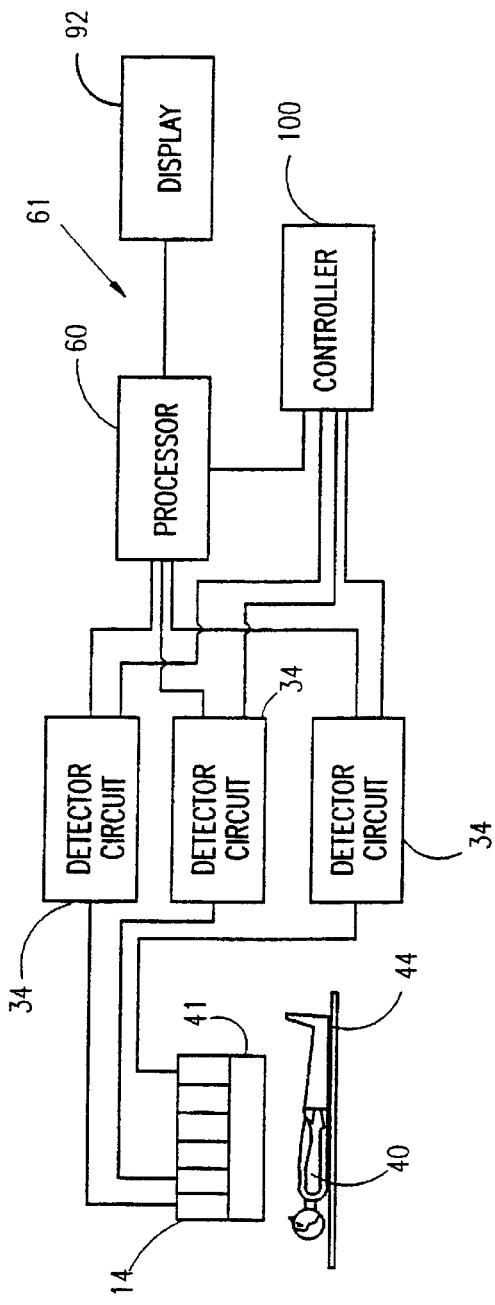
FIG. 3 is a general block diagram of a nuclear medicine imaging system according to a preferred embodiment of the invention.

FIG. 3 is a general schematic of a nuclear medicine system 61 according to a preferred embodiment of the invention. System 61 generally comprises an examination area 44, a detector crystal 41 and a plurality of photomultiplier (PM) tubes 14. When a gamma-ray source is placed in examination area 44, gamma-rays created by a radiation event interact with detector 41 to generate weak scintillations. These scintillations are amplified by PM tubes 14, which also convert the scintillations into electrical signals having an amplitude related to the energy of the interacting gamma-ray. Each of PM tubes 14 is connected to a detector circuit 34, described more fully below. The outputs from circuits 34 are passed to a processor 60 which determines the position of each radiation event from the signals generated in PM tubes 14 and combines these events to form an image. This resulting image is displayed on a display 92. System 61 is generally controlled by a controller 100 which generates controlling and timing signals.

In a typical process of nuclear medicine image acquisition, a patient 40 is injected with or ingests a radio-pharmaceutical and is placed in examination area 44. The radio-pharmaceutical is selectably absorbed by tissues in the patient's body, the amount of absorption being typically dependent on the metabolic processes occurring in the tissues. Decay of the radio-pharmaceutical causes a multiplicity of radiation events which are detected by detector 41. A flash of light generated in detector 41 by each detected event is acquired and amplified by at least one, and typically several, PM tube 14. The signal produced by PM 14 in response to an event is called a pulse signal. The integral of the pulse signal corresponds to the number of photons detected by PM 14, which in turn corresponds to the energy detected by detector 41. Detector 41 may be rotated around the portion of patient 40 that is being imaged so that a tomographic image can be generated.

Figure 4:
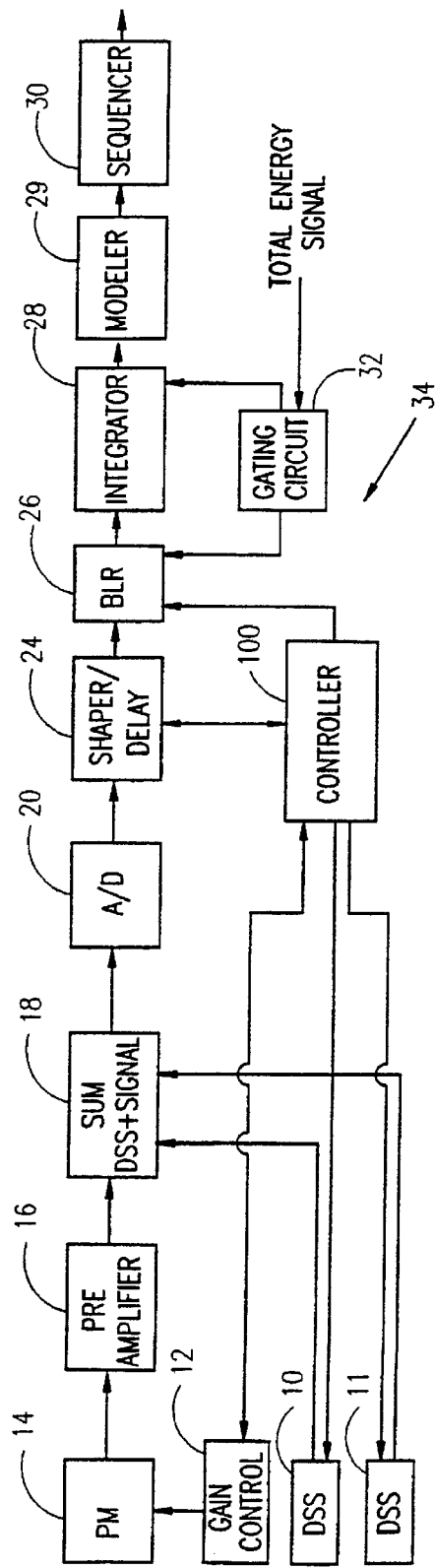
FIG. 4 is a block diagram of a detector circuit of the system shown in FIG. 3.

FIG. 4 show a block diagram of detector circuit 34 according to a preferred embodiment of the present invention. The gain of each PM 14 is controlled by a gain controller 12, since each PM typically amplifies incident light by a different factor. Preferably, gain controller 12 is controlled by controller 100 to compensate for known deviations in the amplification of individual PMs 14. The pulse signal is preferably further amplified by a pre-amplifier 16. Preferably, pre-amplifier 16 performs a small amount of smoothing to reduce noise. Typically, pre-amplifier 16 has a bandwidth of 5–8 MHz. The smoothed pulse signal is digitized by an A/D converter 20 after processing by an adder 18, as described below. It should be noted that A/D converter 20 acquires a number of data samples during each radiation event, so that the pulse signal can be reproduced from the digitized data. Preferably, A/D converter 20 samples at a rate of 20 MHz. The resolution of A/D converter 20 is preferably at least 8 bits, and most preferably 10 bits or more.

The limited resolution of A/D converter 20 can significantly affect the image quality. In a preferred embodiment of the present invention, a resolution enhancement signal is added to the analog signal using adder 18. FIG. 2A shows a series of analog signals generated by a PM in response to radiation events. FIG. 2C, which shares the same time scale as FIG. 2A, shows a preferred resolution enhancement signal.

The effect of the resolution enhancement signal is best explained by the example of the acquisition of a constant signal. For example, assume that one bit step of A/D converter 20 is equal to 8 millivolts. If a constant signal of 15 millivolts is digitized, the digitized signal has the value 1, even though the real equivalent digital value is 1.875, since only the "whole" portion of the signal is digitized. If the constant signal is dithered by a periodic signal with an amplitude of 8 millivolts (one bit), the resulting analog signal is between 7 and 23 millivolts. As a result, the digitized signal is either 1 or 2. If the dithered signal is digitized an infinite number of times, the average digital signal will approach 1.375, since in 7/16 of the cases the signal voltage will be above 16 millivolts and in 9/16 between 8 and 16 millivolts. 0.5 (half a bit) is added to the average signal to reflect the average rounding error of the A/D, i.e., the fact that all values between 8 and 15 millivolts are digitized as 1, even though their average value is 1.5.

Thus, the average acquired value is 1.875. In general, if the signal is digitized a finite number N times, the additional resolution is log(N), if each digitization is performed at a different phase of the periodic dithering signal.

In a preferred embodiment of the present invention, the dithering periodic signal cycles approximately two times during a pulse signal, which is approximately 800 ns.

Preferably, the periodic signal is synchronized to the digitization clock, to ensure that each digitization is at a different phase of the periodic signal. For example, if two added bits of resolution are desired, the digitization frequency is set to be four times the frequency of the periodic signal. The timing of the digitization is set so that within each cycle of the periodic signal, each digitization is at a different phase of the periodic signal. This timing repeats in consecutive signal cycles. Alternatively, a timing scheme which repeats less often than every cycle is used.

The resolution enhancement effect may not be achieved for a single pulse signal, especially if the frequency of the resolution enhancement signal is low compared to the pulse signal. For example, if the resolution enhancement signal cycles only once, and there are two A/D samples in an event, the first sample may be elevated from 1.9 to 2.1, (i.e., from 1 to 2) and the second sample reduced from 1.3 to 1.1 (i.e., not affected). Thus, the total detected energy is 2+(0.5)+1+(0.5)=4.0, compared to the uncorrected value of 1+(0.5)+1+(0.5)=3 and compared to the correct value of 1.9+1.3=3.2, a definite loss of accuracy. However, in a practical system, where the resolution enhancement signal has a higher frequency and where the amplitude of the pulse is non-constant, the accuracy of most all events is increased.

It should be noted that, even if the precision of a single digitization sample is slightly reduced, the cumulative effect of the resolution enhancement signal on many digitized pulse signals yields a higher accuracy of measurement of the pulse signals. It should be appreciated that when the frequency of the periodic signal is higher, in conjunction with a digitization rate as described above, the precision of digitizing a single pulse signal is higher too.

Preferably, the periodic signal is also synchronized to the integration. For example, the integration time of a pulse signal is an integral multiple of the period of the resolution enhancement signal, to ensure that the sum of contributions of the periodic signal to the integrated value is zero. However, if a variable integration time is used, the digital value of the resolution enhancement signal at the sample points is preferably subtracted from the digitized signal, as described below. A useful embodiment of a periodic wave form for variable integration systems is a saw tooth wave.

Since all the calculations after the analog to digital conversion are digital, subtraction of the dither signal can take place before the base-restoration, by correcting each signal, or even after the integration, by subtracting the sum of the resolution enhancement signal at the sample points from the integrated value. Preferably, the value of the resolution enhancement at the sample points is known and does not need to be measured or determined, since the resolution enhancement signal is synchronized to the digitization. Additionally or alternatively, the resolution enhancement signal is controlled by controller 100, as described below.

In a preferred embodiment of the invention, the resolution enhancement signal is produced by a digital sliding scale source 10. Preferably, control and timing signals for digital sliding scale source 10 are generated by controller 100. The amplitude of the resolution enhancement signal is preferably at least as high as a resolution step of the A/D converter 20. The accuracy of the resolution enhancement signal is preferably higher than the desired additional resolution of digitization.

A/D converters do not usually have a linear response over their entire dynamic range. In addition, the linearity of A/D converters changes over time, particularly if the converter is replaced. Some analog to digital conversion systems use a linearity map to correct these non-linearities. However, using a linearity map lowers the accuracy of the digitized signal. In addition, the map needs to be updated periodically, especially if the A/D converter is replaced.

FIG. 2D shows a linearity enhancement signal (not to scale) which is preferably added to the analog signal before digitization. This linearity enhancement signal preferably has a much lower frequency than the resolution enhancement signal, typically 60–100 Hz. The amplitude of the linearity enhancement signal is preferably about 5% of the total range of A/D converter 20. Thus, each radiation event response is digitized in a slightly different region of the dynamic range of A/D converter 20 and non-linearities are averaged out. Because the linearity enhancement signal changes very slowly compared to the duration of a radiation event response, it is perceived as a DC signal by the rest of detector circuit 34.

In a preferred embodiment of the present invention, the linearity enhancement signal is generated by a digital sliding scale source 11 and added to the analog signal by adder 18. The control and timing signal for each digital sliding scale source 11 are preferably generated by controller 100.

Preferably, each detector circuit 34 has its own digital sliding scale source 11 and these sources are not synchronized between different detector circuits. Preferably, each detector circuit 34 also has its own, unsynchronized digital sliding scale source 10. Embodiments of the invention may employ one or both types of enhancement signals.

It should be appreciated that a linearity enhancement signal according to the instant invention is not a baseline restoration signal, as described for example in U.S. Pat. No. 5,508,425 to Goldberg et. al, the disclosure of which is incorporated herein by reference, since the value is not dependent on a preset base-line offset. On the contrary, the linearity enhancement signal purposely introduces a time-varying base-line offset.

In a further preferred embodiment of the present invention, the digital value of the resolution enhancement signal and/or the linearity enhancement signal is subtracted from the digitized signal to lower noise levels in the digitized signal. However, the subtraction is typically not needed.

Since, as described below, the base line of the signal is measured during times when no radiation event is detected, the accuracy of measurement of the base line is enhanced by the resolution enhancement signal. The linearity enhancement signal does not generally add to the accuracy of the measured base line, since it adds a constant to the real base line. However, since the base line signal is continuously updated, the slowly changing linearity enhancement signal acts like part of the real base line for restoration purposes.

In a typical nuclear medicine system, only one radiation event can be processed at a time. It is therefore sometimes advantageous to shorten the processing time of a radiation event. However, the quality of the resulting image is dependent on the integration time of the PM signal. Thus, a shaper-delayer 24 reshapes the digital signal, after it is sampled, to produce a new digital signal with an equivalent energy, but a shorter temporal extent. In effect, the signal is compressed. Preferably, shaper-delayer 24 is controllable by controller 100 to adjustably shape pulses in a parametric manner. Thus, optionally, pulses may be shaped differently as a function of event rate. The use of adjustable pulse shaping improves time resolution and, therefore, higher count rates are possible. It should be noted that although analog shaper-delayers are known in the art, the present invention preferably uses a digital filter to shape/delay.

Before integrating the digital signal to determine the total energy detected by an individual PM 14, it is important to subtract the baseline component of the signal. This baseline is generally equal to the DC signal detected when no events (or scattering events) are occurring, i.e., between pulse signals. Otherwise, a significant proportion of the integrated signal will be from the baseline (offset) component and not the pulse component. A base line restorator 26 is typically used to remove base-line components from the digital signal. Optionally, base line restorator 26 uses inputs from controller 100 to determine the digital value of the resolution enhancement signal and the linearity enhancement signal so that they can also be subtracted from the digital signal. In general, these signals do not need to be subtracted, except as described above. However it has been found that subtracting these values yield a slightly higher accuracy for the integration.

Base line restorator 26 preferably uses a running average scheme to continuously update the base line, i.e., $B(t)=(1/m)*((m-1)*B(t-dt)+Signal(t))$, where $B(t)$ is the baseline at time t, dt is the sampling time and $Signal(t)$ is the input to restorator 26 at time t. Preferably, m, the number of samples, is 256. Alternatively, a moving window scheme is used, i.e., $B(t)=B(t-dt)+(1/n)*(Signal(t)-Signal(t-n*dt))$, where n is the window size.

A gating circuit 32 determines when no radiation events are occurring. Digital signals acquired while no radiation event response is present are entered into the window to estimate the base line for signals acquired while a radiation event response is present.

An integrator 28 is activated by gating circuit 32 to integrate digital signals acquired during a radiation event response. When the radiation event response is over (also determined by gating circuit 32), the integrated signal represents the total amount of energy from the radiation event detected by PM 14.

Gating circuit 32 is used to differentiate between signals which are responses to radiation events and clutter signals such as random noise signals and scattered radiation events. Typically, if the sum of the detected signals from all PMs 14 is outside a specific energy window, the signal is discarded as unusable. Otherwise, it is treated as a valid event, until a further energy value determining step. The sum is determined by adding the pulse signals from all of PMs 14, smoothing the resultant meta-pulse and searching for a peak value, which is compared to an energy window. Preferably, the extent of the energy window is controlled by controller 100 based on the system noise levels, radio-pharmaceutical type and count rate.

Figure 6:
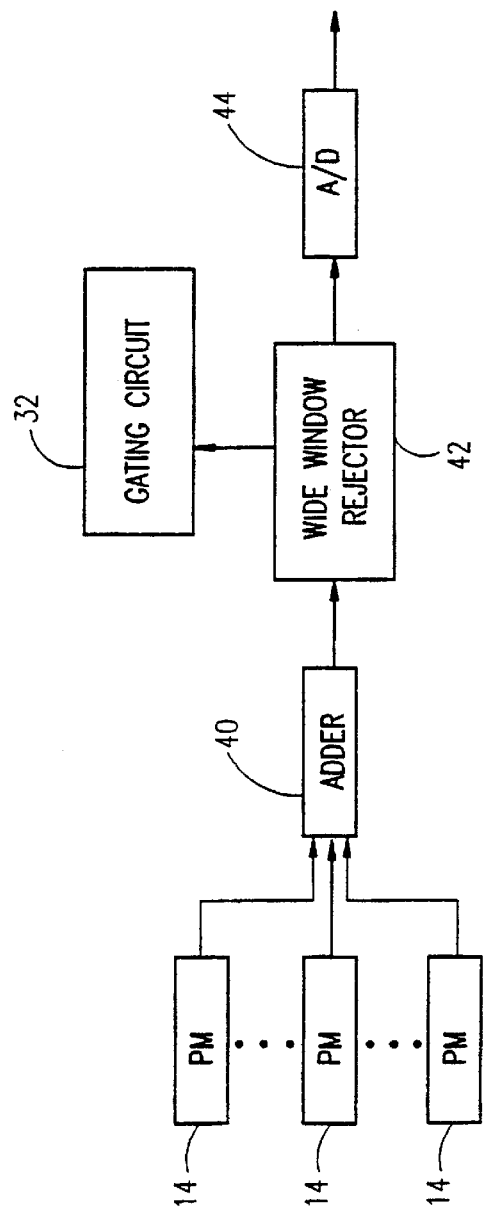
FIG. 6 is a block diagram of gating circuit of the system shown in FIG. 4.

FIG. 6 shows a preferred embodiment of a complete gating apparatus, including an adder 40 which sums the energy readings from all of PMs 14. A wide window rejecter 42 smoothes the sum (which is relatively an analog signal), and determines whether the peak of the energy sum signal is within an amplitude window. If the peak is within the window, rejecter 42 sends an activation signal to gating circuit 32, which is timed to start the integration and the shaping, so that they start at the beginning of the pulse signal and end at its end. It should be noted that the pulse signal to be integrated is delayed by the delayer portion of shaper/delayer 24, to give circuits 40, 42 and 32 time to operate. Preferably, adder 40 sums analog signals, since analog summation is generally more precise than digital summation, for low level signals. The sum is then digitized by an A/D 44 for further use as described herein. Alternatively, the analog signals are digitized before being summed or before being passed to wide window rejecter 42, preferably using the resolution and/or linearity enhancement signals as described above.

In an ideal system, the integrated signal has a linear relationship to the distance of the radiation event from the center of PM 14. However, in real nuclear medicine systems, this relationship is distorted. A main cause of distortion is that PM 14 is more sensitive at its center than near its edges.

Other causes include the difference in refractive index between detector crystal 41 and PM 14 and location dependent variations in detector 41.

Referring again to FIG. 4, in a preferred embodiment of the present invention, the spatial response of PM 14 is modeled by a modeler 29 to correct distortions. The integrated signal is corrected to reflect the value that would have been acquired had PM 14 been optimal. Preferably, all the PMs 14 are modeled using a single empirical (measured) model, usually a look-up-table, preferably a one dimensional look-up table. Alternatively, a mathematical function is used instead of a look-up-table to model the spatial response. Alternatively, the correction model may be two dimensional. Additional or alternatively, each PM 14 can have a different, personalized, model associated therewith.

Preferably, PM modeling is performed in detector circuit 34 by comparing a measured PMC(x,y) to an ideal value PMC(0,0), wherein PMC(x,y) is the response of the tube at to an event which occurs at (an unknown) location (x,y) normalized to the total energy signal from A/D 44. A look-up table is used to determine d/D, the ratio between the distance of the event from the PM center and the distance between two adjacent PMs, based on the difference between PMC (x,y) and PMC(0,0). Once d/D is known, the energy for this pulse signal and all the other pulse signals corresponding to the same event can be corrected as described hereinabove. It should be noted that the total measured energy of the event is previously determined by adder 40.

As an example of the detrimental effects of the uncorrected PM distortion in an Elscint LTD. (Haifa, Israel) 6HR system, the uncorrected flood contrast ratio can be up to 2.0.

Correcting the energy of the individual PM 14 at this point in the process by modeling the photomultiplier response greatly reduces the non-linearities in position determination using Anger arithmetic. Alternatively, the energy is corrected by processor 60 immediately after its receipt of the pulse signal.

Once the pulse signals are integrated and, optionally distortion corrected, they are passed in sequence to processor 60 as components of a single radiation event response (a meta-pulse signal). A sequencer 30 synchronizes and sequences the signals from detector circuits 34 to processor 60.

Figure 5:
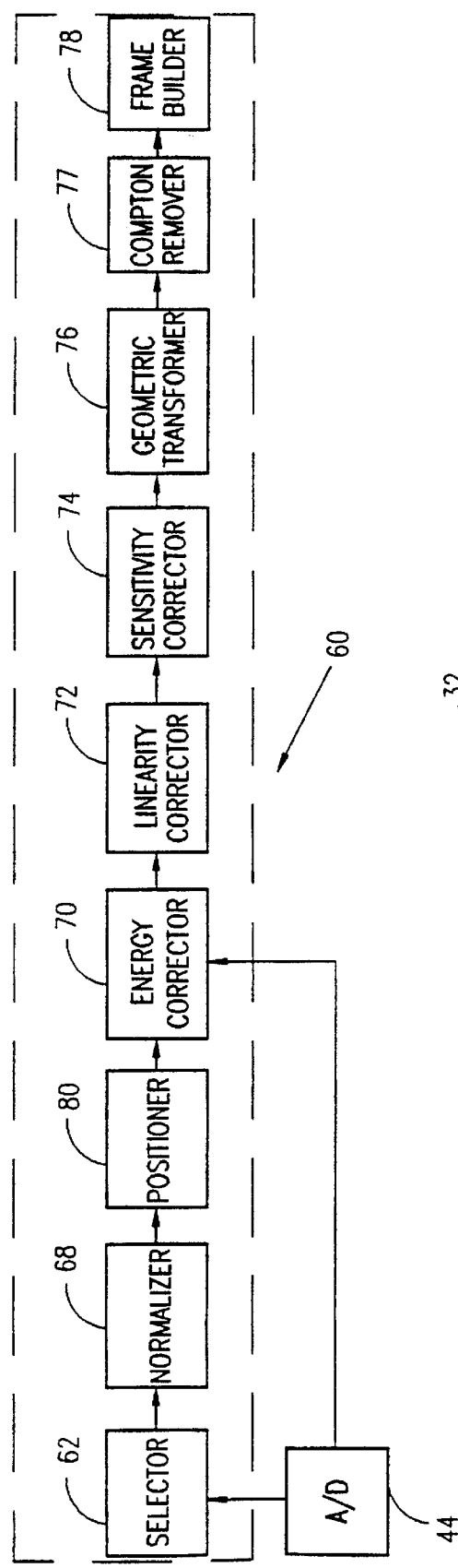
FIG. 5 is a block diagram of a processor of the system shown in FIG. 3.

FIG. 5 is a simplified block diagram of processor 60 which forms a nuclear medicine image based on detected radiation events. Since the image is formed by events, the first step performed by processor 60 is to determine the location of the radiation event in detector crystal 41. A preferred method of event location is called Anger arithmetic and is described in U.S. Pat. No. 3,011,057. However other methods of localization are well known and useful in carrying out the invention, for example, as described in U.S. Pat. No. 5,285,072. The disclosures of both patent documents are incorporated herein by reference.

In order to reduce noise and attain high precision using Anger arithmetic, only relatively strong PM signals are used. A selector 62 selects only those PM signals which are greater than a threshold. Preferably, the height of the threshold is controlled by controller 100 responsive to the total energy (sum of all the signals from adder 40).

As part of the Anger arithmetic, the selected signals are normalized to the sum of the signals generated by all the PMs by a normalizer 68. A positioner 80 calculates the position of the radiation event in detector 41, using Anger arithmetic, based on the selected signals.

The location of the event is now determined. However, if the energy of the event is outside of an energy window, the event is determined to be erroneous and discarded. Similar events may have different acquired energies due to system distortions. Thus, an energy corrector 70 corrects the energy of the acquired event for these distortions before windowing. Alternatively, the energy window is varied as a function of the position of the event.

Among the causes for energy distortions are:
- (a) PM related non-linearities, which are preferably at least partially corrected in a previous step by PM modeling;
- (b) spaces between adjacent PM's 14, which allow some of the energy of the event to escape undetected;
- (c) local imperfections in PMs 14 and in detector crystal 41; and
- (d) events near the edges of detector crystal 41, wherein some of the light associated with the events may escape undetected.

Correcting energy distortions is usually accomplished by calibrating the system to determine calibration data which is stored in a look-up table. The exact energy value is determined by interpolating between table values. Preferably, different look-up tables are used depending on the energy range of the radiation event.

In Anger arithmetic, errors in event energy determination at the PM level are translated to errors in positioning of the event. Thus, after energy correction and windowing, a linearity corrector 72 corrects errors in the localization of radiation events. Preferably, a configuration map, which maps the linearity errors, is used to correct event positions in real-time. Preferably, a continuous approximation such as a spatial B-spline approximation is used to interpolate between map data points. Different linearity correction maps may be used depending on the energy range of the radiation event.

Since different portions of detector crystal 41 have different sensitivities to gamma radiation, an event which occurs in a less sensitive area represents a higher concentration of radio-nuclides than an event which occurs in a more sensitive area. A sensitivity corrector 74 applies this logic by assigning a weight to each event. A high weight is attached to an event which is detected in a less sensitive, low probability area and a low weight is attached to an event which is detected in a more sensitive, high probability area. Preferably, decay of the injected radio-pharmaceutical is corrected for by varying the weight given to each event.

Energy corrector 70, linearity corrector 72 and sensitivity corrector 74 may be applied in other orders than those described above, with appropriate changes to the correction algorithms.

After being corrected, the event is ready for projection onto the image plane. A geometric transformer 76 preferably applies three types of transformations to the event. First, any additional geometric distortions are preferably corrected, as described in further detail below. Second, static transformations such as zooming and rotating are performed, if desired. Third, if detector 41 is moving relative to patient 40, (e.g., during a whole body scan) the event is transformed to its proper, time dependent position in the image plane. Each transformed event is binned to a location in the image plane and individual event characteristics are lost. It should be noted that the image plane might have three or more dimensions, i.e., spatial location in the detector, energy, spatial location of the detector and gating/binning information if physiological binning is used.

A frame builder 78 transforms the events binned in the image plane into a nuclear medicine image. If a three-dimensional image is acquired, for example, utilizing SPECT, frame builder 78 generates a tomographic image from the data binned in the image plane. Frames created by frame builder 78 are then shown on display 92 (FIG. 3).

In a preferred embodiment of the present invention, corrections performed by energy corrector 70, linearity corrector 72, sensitivity corrector 74 and geometric transformer 76 are performed on an event-by-event basis, such that each event has individualized transformations and/or corrections applied to it. In addition, each correction and transformation can be performed independently. In some prior art systems, geometric transformations were combined to form a single static transformation, which was applied in a single calculation step. Applying transformations on an event by event basis has several advantages, including:

(a) it is more precise to transform a floating point event position than a fixed point matrix position;

(b) each event receives a individualized transformation based on its exact characteristics; and (c) changes in imaging parameters, such as changing the zoom factor, do not require recalculation of all of the geometric transformations and corrections, as was the case in prior art systems.

In a preferred embodiment of the invention, the corrections are performed in the following manner:

(a) the positioning system outputs a 14 bit fixed value for the location of the event;

(b) the 14 bit value is converted to a 20 bit value by adding 6 random LSB (least significant bits) thereto;

(c) the 8 MSB (most significant bits) are used to retrieve four gridpoints of a coarse linearity correction map, each gridpoint has a 24 bit floating point value;

(d) the event location is corrected using bi-linear interpolation of the four gridpoints, resulting in a 24 bit floating point value; and (e) the transformations and corrections are applied to the resulting floating point event location.

In a further preferred embodiment of the present invention, Compton scattering artifacts are reduced in real-time, preferably by a Compton remover 77 on an event-by-event basis. A preferred method of Compton scattering artifacts reduction, which is not on an event-by-event basis, is described in U.S. Pat. Nos. 5,293,195 and 5,434,414, the disclosures of which are incorporated herein by reference.

In these patents, all of the events are acquired and grouped into a matrix according to their calculated position, each energy range having a separate matrix. This corresponds to a three dimensional matrix of x, y and E. $N_E(x,y)$ is the number of events in each matrix element, where the element has an energy range E. In local Compton correction, the correct count for each pixel is calculated by multiplying the number of events in a matrix element by a pre-calculated coefficient J(E) and adding the products for all the matrices:

$$N_P^L(x, y) = \sum_E J(E) N_E(x, y) \quad (1)$$

where J(E) is dependent on a system point spread function P(E) and on Compton energy distribution functions $C_m(E)$, both of which are preferably predetermined. $C_m(E)$ are changed to orthogonal form using the well known Graham-Schmidt procedure to yield a vector $\theta_k(E)$ of orthonormal functions, where k is one more than the number of Compton scatter orders chosen in the approximation. As shown in the '414 and '195 patents:

$$J(E) = \frac{P(E) - \sum_k \langle P(E) \cdot \theta_k(E) \rangle \cdot \theta_k(E)}{\langle P(E)^2 \rangle - \sum_k \langle P(E) \cdot \theta_k(E) \rangle^2} \quad (2)$$

In semi-local correction, the count in a pixel element is also dependent on the events detected in neighboring pixels. The size of the neighborhood (S) depends on the desired noise reduction and on available computer power. Image sharpness is not substantially affected by the neighborhood size (within reasonable bounds) because the Compton energy distributions decrease slowly with the distance from the (central) pixel element. The Compton distribution thus results in a point spread function having a sharp peak and low, broad edges. The corrected count is calculated by:

$$N_P^{SL}(x, y) = \sum_E A_1(E) \cdot N_E(x, y) + \sum_E A_S(E) \cdot N_E^S(x, y) \quad (3)$$

where $$A_1(E) = \frac{P(E)}{\langle P(E) \rangle^2} \quad (4)$$

$$A_S(E) = \frac{(J(E) - A_1(E))}{S}$$

and $N_E^S(x,y)$ is the count of events in all of area S at energy level E.

As can be appreciated, semi-local Compton scatter correction is especially important when searching for cold-spots in a hot region. In such a case, the broad point spread function which is caused by the Compton scattering may hide the cold-spot by completely obliterating any contrast between the hot areas and the cold-spot.

Using the same pre-calculated coefficients as in the above patents, in a preferred embodiment of the present invention, the events are corrected for Compton artifacts on an event-by-event basis, rather than after the fact. This results in a considerable increase in image quality since the Compton correction is not performed on a small number of discrete energy windows, but may be performed as a continuous function of energy. A further advantage of event-by-event correction is that once all the events are acquired, the image is Compton free, without the necessity of performing additional processing on the image.

In order to perform an event-by-event correction it must first be realized that multiplying an event count by a scalar coefficient is functionally equivalent to multiplying each event by a different, energy dependent, weight. In local correction, the weight is simply J(E). In semi-local correction, the two required weights can be calculated by first converting equation (3) into a form where the contribution of the (center) pixel is separate from the contribution of the neighboring pixels (all the variables and parameters are as described above):

$$N_P^{SL}(x, y) = \quad (5)$$
$$\int_E A_1(E) \cdot N(E, x, y) dE + \int_E \frac{J(E) - A_1(E)}{S} \cdot N(E, x, y) dE +$$
$$\int_E \frac{J(E) - A_1(E)}{S} \cdot N^{S'}(E, x, y) dE$$

So $$N_P^{SL}(x, y) = \int_E w_1(E) \cdot N(E, x, y) dE + \int_E w_S(E) \cdot N^{S'}(E, x, y) dE \quad (6)$$

$$\text{and } w_1(E) = \frac{J(E) + (S-1)A_1(E)}{S} \quad (7)$$

$$w_{S'}(E) = \frac{J(E) - A_1(E)}{S}$$

where N(E,x,y) is a continuous function of E, x and y, giving the number of counts at location (x,y) having an energy E and $N^{S'}$(E,x,y) is the number of counts in area S, not including the central pixel.

In a preferred embodiment of the invention $w_1$(E) and $w_{S'}$(E) are pre-calculated based on J(E), P(E) and S. A 32 bit fixed point matrix, having 16 bits for the integral portion and 15 bits for the fractional portion is preferably used (+one bit for the sign) to accumulate the events. Each event is entered at its location (x,y) with a weight $w_1$(E) and values $w_{S'}$(E) are entered at several, preferably 8 neighboring pixels. Thus, each event is individually convoluted with a filter having energy dependent weights. The weight in the center pixel is usually different from the weights in the surrounding pixels. Alternatively, only local correction is performed, using a single weight J(E) (zero dimension convolution). It should also be appreciated that the size and shape of area S and the weights $w_1$ and $w_{S'}$ may be varied. In particular, if a larger areas S is used, the weight assigned to distant (from the center) pixels may be different (lower) then the weights assigned to pixels near the central pixels. In addition, Compton scatter correction can also be used to reduce other unwanted radiation events whose energy-dependent distribution is known, such as lead X-ray events which are caused by the interaction of Gamma rays with the lead collimator and/or by fluorescence. Further, in multi-energy systems, a different set of weights may be used for each type of primary radiation event (isotope). If simultaneous imaging at two energies is performed it may be difficult to correct Compton scatting for both energies. In one preferred embodiment of the invention, Thallium$^{201}$ is used as a radioactive source. Thallium$^{201}$ has two main emission energies, 75 kev and 170 kev. In this embodiment, any detected event having an energy below 75 kev is assumed to originate from a 75 kev type event and not from a 170 kev type event.

It should be understood that the above calculation (equation 7) results in the ratio between $w_1$(E) and $W_{S'}$(E) being energy dependent. It should also be noted that the ratios are not dependent on the collimator used. This energy dependence reflects the dependence of the Compton distribution on the energy of the event. It should be appreciated that the Compton scatter distribution functions $C_m$(E) may be approximated to any desired degree, by using only a limited number of orders of scattering or by using a polynomial approximation, for example as in U.S. Pat. No. 4,839,808 to Koral, et al., the disclosure of which is incorporated herein by reference.

It should be appreciated that all of the above described corrections and transformations can be changed during processing, responsive to input from an operator or other sources of information. For example, if one frame acquisition time is found to be shorter than another frame acquisition time, the events in the shorter frame are given a higher weight.

In another preferred embodiment of the present invention, an event counter is used to count the approximate number of real events. If a lower number of radiation events is processed by system 61, than the actual number of events, due to count rate limitations, the weight of processed events is increased to compensate.

In yet another preferred embodiment of the present invention, a parallel beam image is simulated using a fan beam collimator by applying a geometric transformation to each event. Parallel beam simulation is useful when a fan beam collimator is used to acquire an image of a small organ, but it is desirable to view an undistorted image which utilizes the image plane more efficiently. As noted above, the image plane has a limited spatial resolution, to best utilize it, the region of interest should fill up as much of the image plane as possible. To effect this simulation, an organ is imaged using a fan beam collimator. Each event is transformed by geometric transformer 78 to correct for the distortions caused by the fan beam collimator. It should be noted that this transformation is applied before tomographic processing of the events, in the frame builder 78.

In a further preferred embodiment of the present invention, variable mechanical misalignments are corrected in real-time.

In some imaging procedures, detector 41 is moved along an axis of patient 40. If the speed of motion is not constant, portions of patient 40 which are scanned faster appear have less events than portions which are scanned more slowly. In a preferred embodiment of the present invention, each event is given a weight depending on the actual speed of the scanning; a higher weight for fast scanning and a lower weight for slow scanning.

Figure 7:
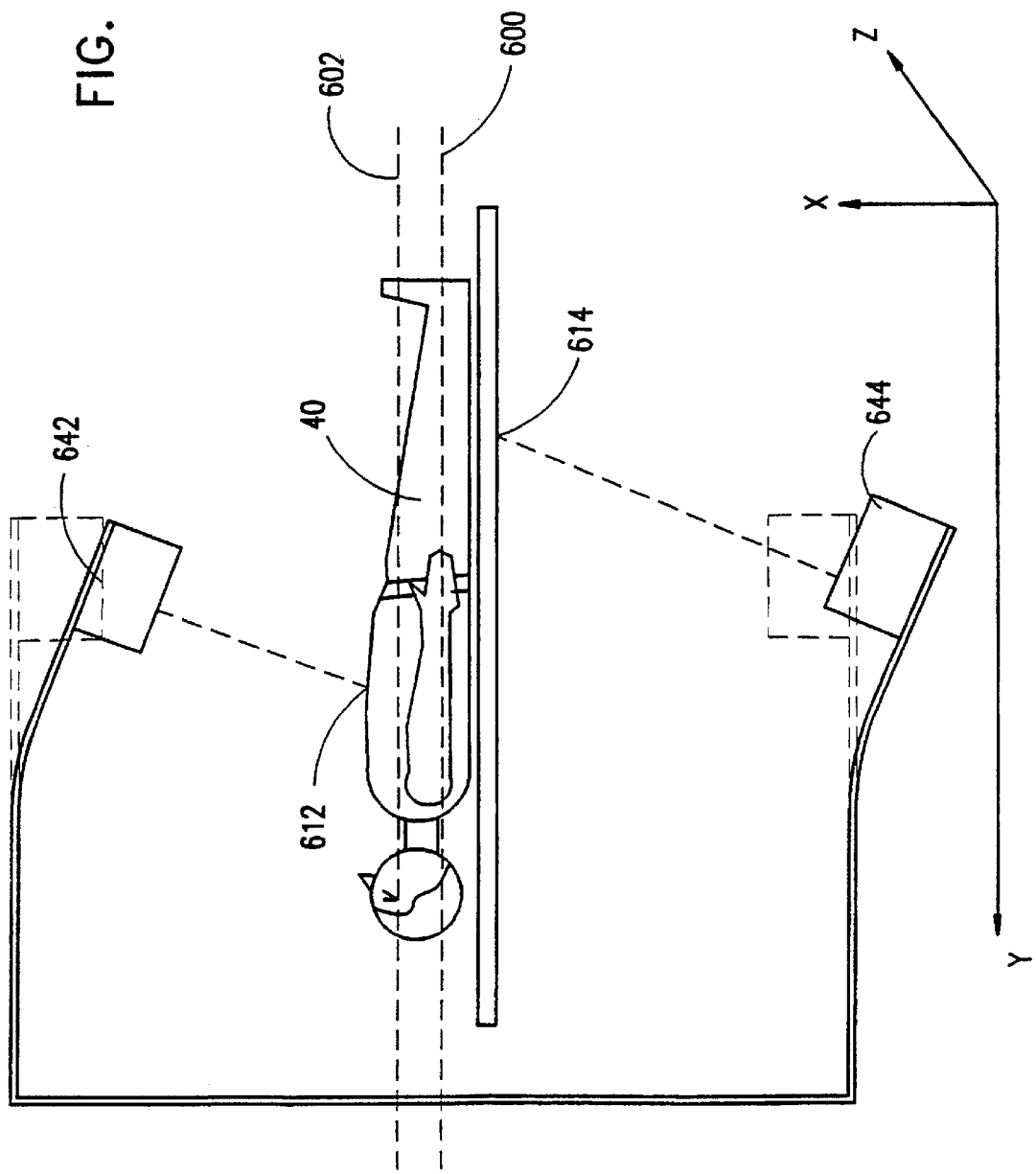
FIG. 7 illustrates, in an exaggerated manner, the effect of sagging on a detector crystal imaging a patient.

FIG. 7 shows (in exaggerated form) another type of mechanical misalignment. Patient 40 has a Y axis along his body and an X-Z plane bisecting it. A nuclear camera 642 is rotated around patient 40, to capture events for forming a tomographic image. A first misalignment to be corrected is y-axis rotation misalignment. Due to the great weight of camera 642, an actual center of rotation 602 is different from a configured center of rotation 600. In addition, camera 642 sags either towards or away from the center of rotation as a function of the rotation angle. This misalignment is corrected in a preferred embodiment of the present invention by applying an angle dependent geometric transformation, to each event so that it is moved in the X-Z plane. This transformation is applied by geometric transformer 76.

A second misalignment is axial (line of sight) missregistration. As mentioned above, camera's 642 weight causes it to sag. However, when camera 642 is above patient 40, it sags towards him and when a nuclear medicine camera 644 is below him, it sags away from him. Since, the cameras are mounted on long beams, which bend so that the cameras viewing angle changes, the line of sight of the camera moves along the Y-axis of patient 40 as the amount of sagging changes. In a preferred embodiment of the present invention, this misalignment is corrected by applying an angle dependent geometric transformation to each event so that it is moved along the Y-axis.

Mechanical misalignments are typically detected either by configuration data, by feedback from mechanical position, velocity or acceleration sensors, or by processing the acquired data to find correlations and Fourier frequency peaks which correspond to certain types of misalignments. For example, y-axis rotation misalignment (described above), manifests itself as a Fourier frequency peak which corresponds to the degree of misalignment.

In yet another preferred embodiment of the invention geometric transformations applied to an event are dependent on a measured biological rhythm, such as stomach contractions, breathing or heart beat.

It should be noted that all of the abovementioned corrections are preferably done in real-time on an event by event basis. Performing calculations on individual events in real-time produces high accuracy results without the data-storage penalty required if all the events are stored for off line processing.

It should be appreciated that within the context of the present invention, a look-up-table and a mathematical formula can sometimes be interchanged with respect to function. However, a mathematical function is inherently more precise than a look-up-table, albeit, slower and not as capable of being easily recalibrated.

It should also be appreciated that processor 60, as described herein can be used with an analog front end, although a digital front end as described is preferred.

It will be appreciated by persons skilled in the art that the present invention is not limited to what has been thus far described. Rather, the scope of the present invention is limited only by the following claims:

What is claimed is:

1. A method of reducing artifacts, caused by generation of unwanted photons by scattering of photons generated from primary events, in a radiation camera, comprising:

(a) detecting a radiation event;
   (b) determining an energy of said event;
   (c) determining a location of said event;
   (d) convoluting a weight associated with each event on an event-by-event basis with a spatial filter function, such that the weight associated with the event is distributed over an area including the location of the event, wherein the relative weight distribution between different locations in the area is dependent on the determined energy and wherein the relative weight distribution at one determined energy is different from that at a second determined energy when both determined energies are associated with a primary event having the same energy;
   (e) repeating (a)–(d) for a plurality of events; and
   (f) reconstructing an image from the distributed weights.

2. A method in accordance with claim 1, wherein the filter function is a matrix having matrix element values and wherein the weights are distributed into an image plane based on the matrix.

3. A method in accordance with claim 2, wherein the matrix has a first element having a first value and a second element having a second value and wherein the ratio between the first and second values is energy dependent.

4. A method in accordance with any of claims 1–3, wherein said filter function is dependent on a predetermined energy dependent scatter coefficient of the unwanted photons in the radiation camera.

5. A method in accordance with any of claims 1–3, wherein the relative weight distribution of the filter function has a continuous dependence on the energy of the event.

6. A method in accordance with any of claims 1–3, wherein the relative weight distribution of the filter function is dependent on the energy of the primary radiation event.

7. A method in accordance with claim 6, wherein the primary radiation events are generated by one of at least two different radioactive elements introduced into a patient.

8. A method in accordance with any of claims 1–3, wherein the unwanted photons comprise Compton scattered photons of a primary event.

9. A method in accordance with any of claims 1–3, wherein the unwanted photons comprise x-rays generated by the interaction of a primary event with the radiation camera.

10. A method according to claim 1, wherein said weight and said relative weight distribution is independent of a collimator used for said detection.

11. A nuclear medicine system which images radiation from primary radiation events and which detects unwanted photons having a known energy distribution, comprising:

an event detector which detects a radiation event;
   an event energy and location detector which determines the energy and location of the event;
   an unwanted-photon corrector which receives an event energy and location and convolutes a weight associated with the event with an energy dependent spatial filter function; and
   an image reconstructor which reconstructs an image based on the convoluted events,
   wherein the relative weight distribution of the filter function at one energy is different from the relative weight distribution of the filter function at a different energy associated with a primary event having the same energy.

12. A system in accordance with claim 11, wherein the filter function is a matrix having matrix element values and wherein weights associated with an event are distributed into an image plane based on the matrix.

13. A system in accordance with claim 12, wherein the matrix comprises a first element having a first value and a second element having a second value and wherein the ratio between the first and second values is energy dependent.

14. A system in accordance with any of claims 11–13, wherein different filter functions are used for events associated with different primary event types.

15. A system in accordance with any of claims 11–13, wherein the unwanted photons comprise Compton scattered photons of a primary event.

16. A method in accordance with any of claims 11–15, wherein the unwanted photons comprise x-rays generated by the interaction of a primary event with the radiation camera.

* * * * *